US006393905B1

(12) United States Patent
Steele (10) Patent No.: US 6,393,905 B1
(45) Date of Patent: May 28, 2002

(54) ADHESIVE TESTING APPARATUS

(76) Inventor: Jonathan M. Steele, 2814 Carriage Rowe, Duluth, GA (US) 30096

( * ) Notice: Subject to any disclaimer, the term of this patent is extended or adjusted under 35 U.S.C. 154(b) by 0 days.

(21) Appl. No.: 09/418,300

(22) Filed: Oct. 14, 1999

Related U.S. Application Data
(60) Provisional application No. 60/108,343, filed on Nov. 13, 1998.

(51) Int. Cl.$^7$ ............................................. G01N 19/04
(52) U.S. Cl. ...................................... 73/150 R; 73/827
(58) Field of Search .......................... 73/150 R, 150 A, 73/827; 81/472, 477

(56) References Cited

U.S. PATENT DOCUMENTS

| | | | |
|---|---|---|---|
| 3,282,094 A | 11/1966 | Hinden | 73/150 |
| 3,527,093 A | 9/1970 | Sellers | 73/150 |
| 3,678,738 A | 7/1972 | Jubelt | 73/88 B |
| 3,718,039 A | 2/1973 | Bacon et al. | 73/141 AB |
| 4,027,529 A | 6/1977 | Olsen | 73/88 B |
| 4,195,589 A * | 4/1980 | Blattner | 116/212 |
| 4,641,521 A * | 2/1987 | Lawrence | 73/161 |
| 5,361,639 A | 11/1994 | Thorsen | 73/827 |
| 5,452,617 A * | 9/1995 | Brown | 73/862.23 |
| 5,649,447 A | 7/1997 | Van Avery | 73/150 A |
| 5,703,302 A | 12/1997 | Hasler et al. | 73/865.8 |
| 6,050,140 A * | 4/2000 | Koch | 73/150 A |

FOREIGN PATENT DOCUMENTS

| | | | |
|---|---|---|---|
| GB | 2330813 | * | 5/1999 |
| SE | 7209405-5 | | 9/1975 |

OTHER PUBLICATIONS

Proceq SA, Pull–off Tester DYNA, (1988).
KTA–TATOR, INC., Adhesion Testing Instruments (date unknown).
Steele, Jon & Jay, Critical Performance Characteristics For Corrosion Barrier Coatings Applied to Concrete (Nov. 1998).
Steele, Jon, Testing Adhesion of Coatings Applied to Concrete, 33 Materials Performance, No. 11, pp. 33–36 (1994).

* cited by examiner

Primary Examiner—Daniel S. Larkin
(74) Attorney, Agent, or Firm—Gardner Groff & Mehrman, P.C.

(57) ABSTRACT

A test device, a testing method, and a test dolly for measuring the adhesion strength of a coating applied to a substrate. The test dolly is attached to the coating, the dolly is coupled to the testing device, and progressively increasing force is applied to the testing device until the dolly breaks free. The testing device includes a beam and engagement features, forming a lever arm about a fulcrum comprising a rocker or other contact surface resting upon the coated substrate, to impart a force on the dolly normal to the coated surface. An indicator measures the force required to detach the dolly from the substrate. The dolly has a straight-sided base portion.

22 Claims, 3 Drawing Sheets

ADHESIVE TESTING APPARATUS

CROSS REFERENCE TO RELATED APPLICATION

This application claims the benefit of U.S. provisional patent application No. 60/108,343, filed Nov. 13, 1998, hereby incorporated by reference herein in its entirety.

BACKGROUND OF THE INVENTION

1. Field of the Invention

The present invention relates generally to materials testing, and more particularly to a device and method for measuring the adhesion strength of a coating to a substrate.

2. Description of Related Art

A variety of coatings are commonly applied to surfaces of substrates to enhance or otherwise alter characteristics of the substrate. For example, coatings such as corrosion barriers, paint, adhesives, moisture barriers, vapor barriers, and sheet materials are often applied to substrates formed of materials such as metals, cementitious materials, wood, or plastics.

The durability and longevity of a coating is highly dependent on the strength of the adhesion to the substrate over which it is applied. The ability to measure the adhesion strength of coatings is a useful quality control criterion that is sometimes used for acceptance or rejection of coatings application work, and/or to compare the relative qualities of different coating materials. Also, preliminary coating adhesion testing can be used to evaluate a substrate surface to determine if additional surface preparation is needed before applying a final coating to the substrate. See, e.g., Jon Steele and C. Jay Steele, *Critical Performance Characteristics for Corrosion Barrier Coatings Applied to Concrete*, and Jon Steele, *Testing Adhesion of Coatings Applied to Concrete*, 33 MATERIALS PERFORMANCE 33–36 (November 1994, NACE, International), both of which are incorporated herein by reference for background information regarding coating adhesion testing.

Currently, there are few effective methods of determining coating adhesion, especially the adhesion of coatings applied to concrete substrates. Many of the coating adhesion test devices that are currently available have been found to be unwieldy in use and unduly complex and expensive, especially for routine testing in the field. As a result, effective quality control of coating application and adhesion is often overlooked. Thus, it can be seen that needs exist for improved methods and devices for testing the adhesion of a coating to a substrate. It is to the provision of methods and devices meeting these and other needs that the present invention is primarily directed.

SUMMARY OF THE INVENTION

The present invention provides a testing apparatus and method for testing the adhesion of a coating to a surface. The invention also includes an improved testing dolly for use with the testing apparatus and method of the present invention. According to preferred forms, the apparatus and method of the present invention are simple, rugged, and inexpensive to manufacture and use, are readily adaptable to a wide variety of uses, and provide effective and accurate testing results.

Briefly described, in a preferred form, the present invention comprises a device for testing the adhesion of a coating to a substrate. The device preferably includes a beam having a first end, a second end, and an intermediate portion. The device preferably also includes a contact head connected to the first end of the beam. The device preferably also includes a pointer arm having a first end connected to the first end of the beam and a second free end opposite the first end. The device preferably also includes a scale mounted to the beam proximal the second end of the pointer. The device preferably also includes engagement means connected to the contact head for engaging a test dolly.

Otherwise defined, the present invention provides a device for testing the adhesion of a coating to a substrate, the device preferably including a beam having a first end, a second end, and an intermediate portion, a contact head connected to the first end of the beam, engagement means connected to the contact head for engaging a test dolly, and an indicator for indicating a magnitude of force applied by the device.

Still another aspect of the present invention provides a method of testing the adhesion of a coating to a substrate. The method preferably includes attaching a test dolly to a portion of a coating. The method preferably further includes coupling a testing device to the test dolly, the testing device comprising a beam, a contact head connected to a first end of the beam, engagement means for engaging the test dolly, and an indicator. The method preferably further includes applying sufficient force to a second end of the beam to detach the test dolly and an attached portion of the coating from the substrate. The method preferably further includes observing the indicator to determine a measure of adhesion of the coating to the substrate.

Still another aspect of the present invention provides a test dolly for testing the adhesion of a coating to a substrate. The test dolly preferably includes a base portion having an attachment face for adhesion to a portion of a coating, the base portion further including a plurality of straight sides. The test dolly preferably further includes an engagement feature for attachment to a testing device.

These and other features and advantages of the present invention are described herein with reference to the drawing figures, or will be readily apparent to those skilled in the art having been provided with the teaching herein.

DETAILED DESCRIPTION

Referring now to the drawing figures, wherein like reference numerals represent like parts throughout, the testing device and method, and the test dolly of the present invention will now be described with reference to preferred embodiments. It is to be understood that the embodiments described and depicted herein are intended as examples to provide an understanding of the invention, but that the invention is not limited to the specific embodiments described. It must also be noted that, as used in the specification and the appended claims, the singular forms "a," "an" and "the" include plural referents unless the context clearly dictates otherwise.

A first preferred embodiment of the testing device 10 of the present invention is shown in FIGS. 1–5. The device 10 preferably comprises a beam 12 having a first end 14, a second end 16, and an intermediate portion 18 extending between the first and second ends. The beam 12 preferably comprises a rod of substantially rigid material permitting a degree of resilient flexure upon the application of a bending moment thereto. For example, the beam 12 can comprise a length of spring steel rod stock. The beam 12 can have a round (depicted), square or otherwise shaped cross-section. In example embodiments, the beam 12 is formed to have a diameter of between about ¼" to about 1", and a length of between about 12" to about 36". A diameter of about ½" and a length of about 24" has been found to provide particularly advantageous results for testing the adhesion of a variety of coatings to a cementitious substrate. Of course, the dimensions and selection of materials will vary depending upon the intended application, and may be greater than or less than the example dimensions particularly described herein, as may be readily determined by one of ordinary skill in the art.

The first end 14 of the beam 12 is preferably connected to a contact head 20. The contact head can comprise an integral portion of the beam 12, or can be formed as a separate component and permanently or releasably connected to the beam. For example, in the embodiment depicted in FIGS. 1–5, the contact head 20 comprises a generally cylindrical element having a circumferential face 22 and first and second sides 24, 26, and is directly connected to the beam 12. When placed in contact with a support surface, the circumferential face 22 permits a "rocking" motion, wherein the point of contact of the circumferential face with the support surface forms a fulcrum for pivotal motion of the device 10 thereabout. In the alternate embodiment depicted in FIGS. 6–7, the device 10' comprises a contact head 20' that is indirectly connected to the first end of the beam 12' through a pivot pin 27 and an engagement head 28. The beam 12' is secured within a hole formed in the engagement head 28, and the engagement head 28 is pivotally coupled to the contact head 20' by means of the pivot pin 27, which is attached to the contact head 20' and extends through a bore in the engagement head 28. In this embodiment, the contact head 20' provides a fixed point of contact with a support surface, and the pivot pin 27 forms a fulcrum for pivotal motion of the device 10' thereabout. It may be necessary to provide the contact head 20 with one or more holes or other gripping or clamping features (unshown) to hold the part during fabrication.

One or more beam couplings can be provided for releasably coupling the beam 12 and the contact head 20. Alternatively, the beam 12 can be permanently coupled to the contact head 20, for example, by welding, adhesive, friction fit, or integrally forming the contact head 20 as the end portion of the beam 12. As seen best with reference to FIG. 1A, a first beam coupling in the form of a first hole 30 in the circumferential face 22 of the contact head 20 engages the first end 14 of the beam 12 in a first beam position depicted in FIG. 1. A second beam coupling in the form of a second hole 32 can optionally be provided in the circumferential face 22 of the contact head 20, angularly offset from the first hole 30, to engage the first end 14 of the beam 12 in a second beam position depicted in FIG. 2. One, two, or more beam couplings can be provided, allowing the contact head 20 to be selectively connected to the beam 12 in any of a plurality of angularly offset positions.

The device 10 preferably further comprises engagement means for engaging a test dolly 40. The engagement means can be directly connected to the contact head 20, as by welding, adhesive, mechanical fasteners or integrally forming the engagement means as part of the contact head 20. For example, in the embodiment depicted in FIGS. 1–5, the engagement means comprises at least one flange 42 (two flanges 42 are depicted), extending from the contact head 20. Each flange 42 preferably comprises a through hole 44 for removably receiving a removable pin 46 adapted to engage a cooperating hole 48 in the test dolly 40. Insertion of the pin 46 through the hole(s) of the flange(s) and the hole 48 of a test dolly 40 releasably engages the test dolly to the test device 10. Removal of the pin 46 disengages the test dolly 40 from the device 10. The pin 46 is preferably round, and has an outer diameter slightly smaller than the diameter of the hole 48 of the test dolly 40, so that the pin can freely rotate within the hole 48, thereby reducing or eliminating any tendency to apply a twisting or peeling force to the test dolly upon use of the testing device. A lanyard 49 or other retention means can be provided to prevent inadvertent loss of the pin 46.

Figures 6, 7, 8:
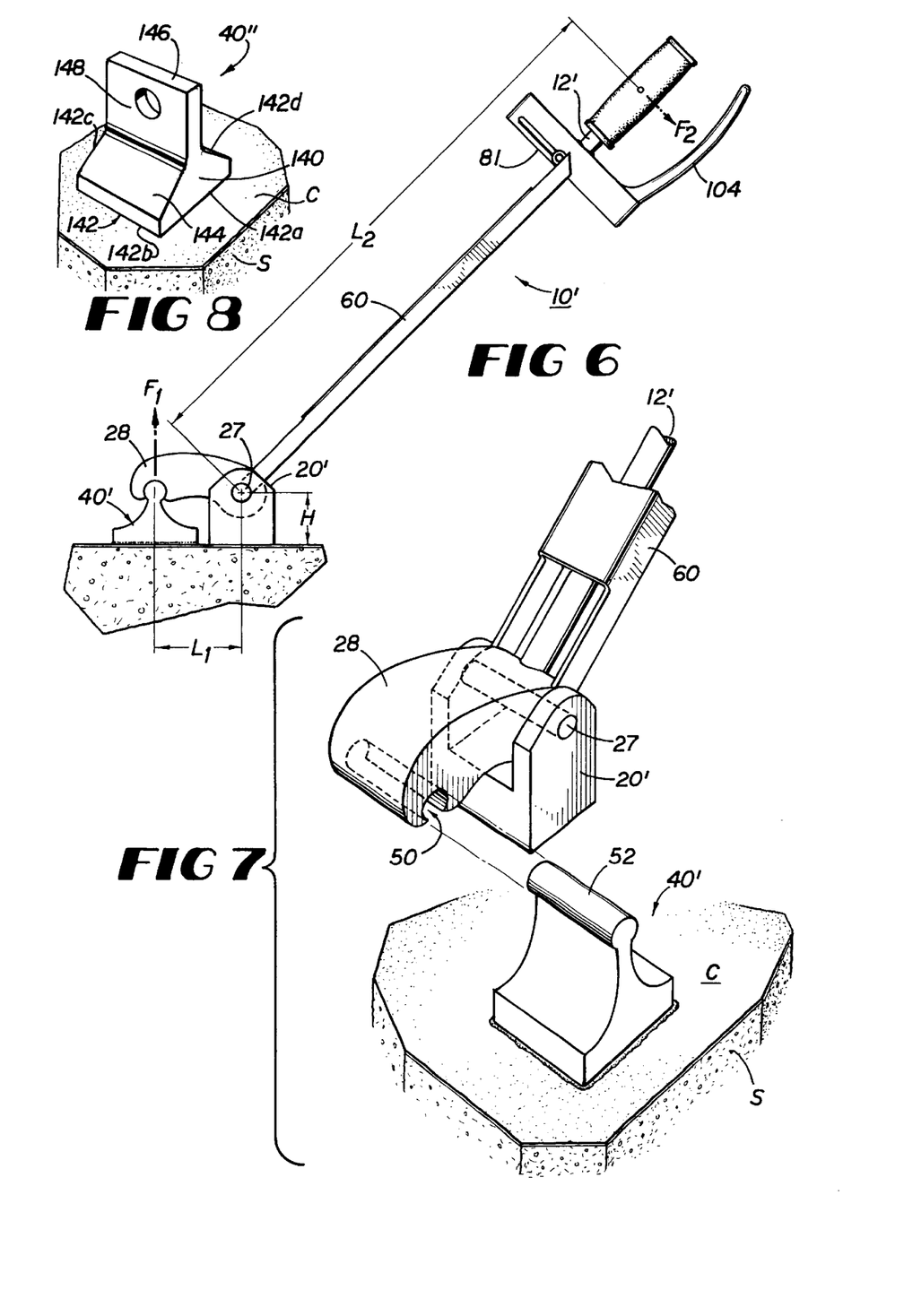
FIG. 6 shows a side view of a testing device according to another preferred form of the present invention.
FIG. 7 shows a perspective view of a portion of the testing device of FIG. 6, detached from a test dolly according to a preferred form of the present invention.
FIG. 8 shows a test dolly according to a preferred form of the present invention.

In the alternate embodiment shown in FIGS. 6–7, the engagement means comprises a surface feature of the engagement head 28 adapted to releasably engage a cooperating surface feature of a test dolly 40'. For example, in the depicted embodiment, the surface feature of the engagement head 28 comprises a slot 50 having a generally circular profile and extending longitudinally at least partially through the engagement head. The corresponding surface feature of a test dolly 40' comprises a generally circular key 52 extending longitudinally along at least a portion of the dolly. The key 52 can be engaged within the slot 50 by longitudinally sliding the end of the key into the end of the slot and advancing the key at least partially into the slot. Engaged in this manner, the cooperating shapes of the key 52 and slot 50 permit the engagement head 28 to apply outward force to the test dolly, while the generally circular shapes of the cooperating surface features permit a degree of pivotal movement of the engagement head 28 about the axis of the key 52 to reduce or eliminate any tendency to apply a twisting or peeling force to the test dolly. The key 52 is released from the slot 50 by retracting the key from the slot in a longitudinal direction. In alternate embodiments, the arrangement of the cooperating surface features can be reversed, with the key provided on the engagement head and the slot in the test dolly. In still further alternate embodiments, the engagement means can comprise other forms of releasable engagement means such as, for example, interengaging threads, ball-and-socket connectors, hooked or offset features, magnetic connections, connector links, interengaging projections and recesses, and/or other types of cooperating surface features; or, less preferably, can comprise permanent engagement means such as adhesives, welding, mechanical fasteners, or forming the test dolly and the testing device as integral, unitary components.

The testing device 10 of the present invention preferably further comprises an indicator for indicating the magnitude of force applied by the device to a test dolly 40. In preferred form, the indicator comprises a pointer arm 60 having a first end 62 substantially rigidly connected to the first end 14 of the beam 12, and a second free end 64. The pointer arm 60 can be directly connected to the beam 12, or can be indirectly connected to the beam through one or more intermediate elements such as, for example, the contact head 20 or the engagement head 28. One or more pointer couplings can be provided for releasably coupling the pointer arm 60 and the beam 12. Alternatively, the pointer arm 60 can be permanently coupled to the beam 12, for example, by welding, adhesive, friction fit, or integral forming. The pointer arm 60 preferably comprises a generally C-shaped channel, preferably formed of a stiffened steel or other metal, adapted to at least partially overlie or surround a portion of the beam 12, as seen with reference to FIGS. 5 and 5A. A cushion 66, such as a rubber or cork pad can be provided between the pointer arm and the beam to absorb impact resulting from the device 10 snapping back from a flexed position to its relaxed state upon detachment of the test dolly 40 from a substrate. In preferred form, the cushion is affixed, as by adhesive, to the inner wall of the intermediate leg 67 of the C-channel of the pointer arm 60, at least at a location proximal the second end 64 of the pointer arm. The intermediate leg 67 of the C-channel of the pointer arm 60 is preferably removed at the first end 62 and second end 64, whereby the side legs 68, 69 comprise forked ends.

Figures 1, 1A:
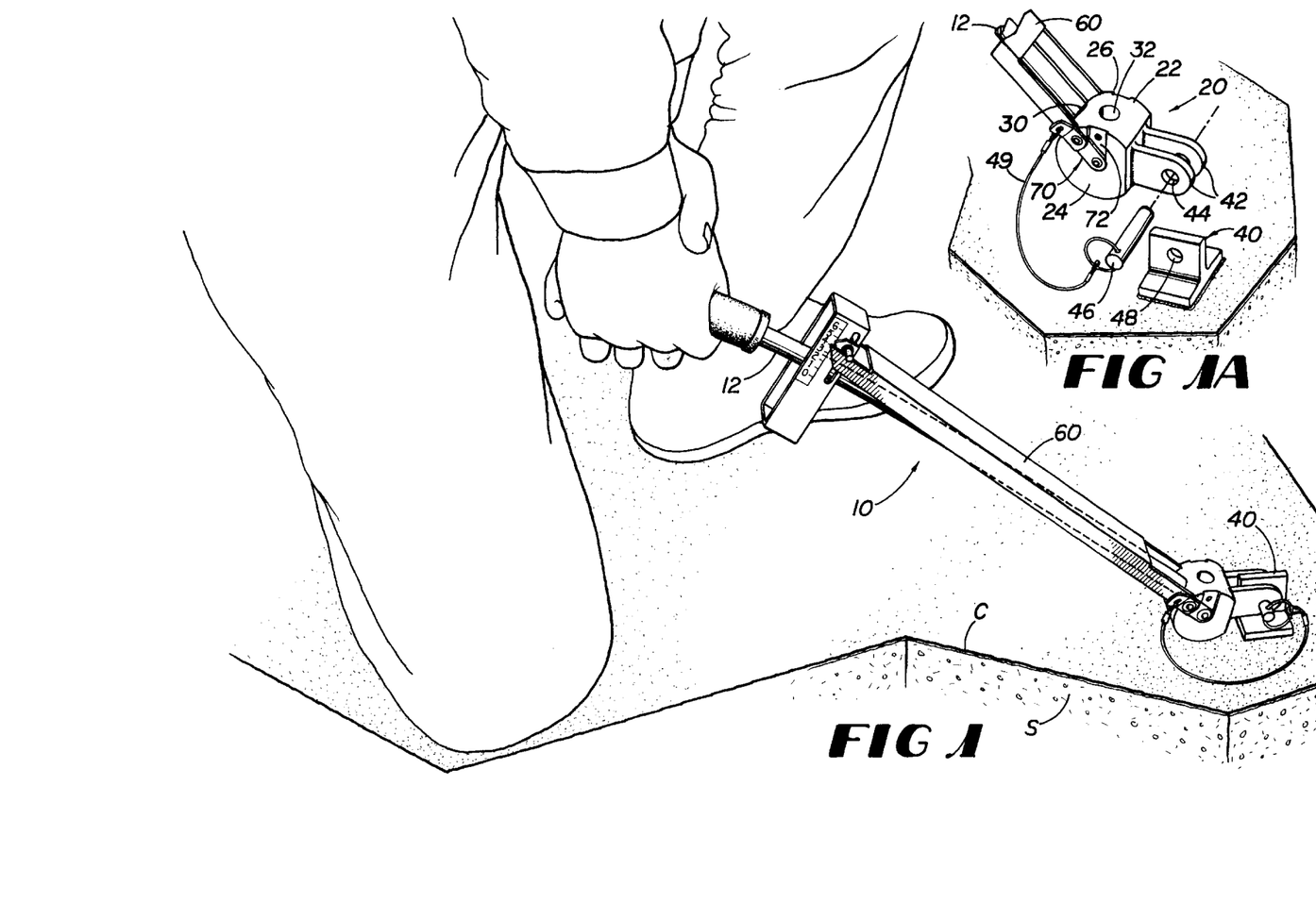
FIG. 1 shows a perspective view of a testing device used to test the adhesion of a coating to a generally horizontal substrate according to a preferred form of the present invention.
FIG. 1A shows a portion of the testing device of FIG. 1, detached from a test dolly according to a preferred form of the present invention.
Figure 2:
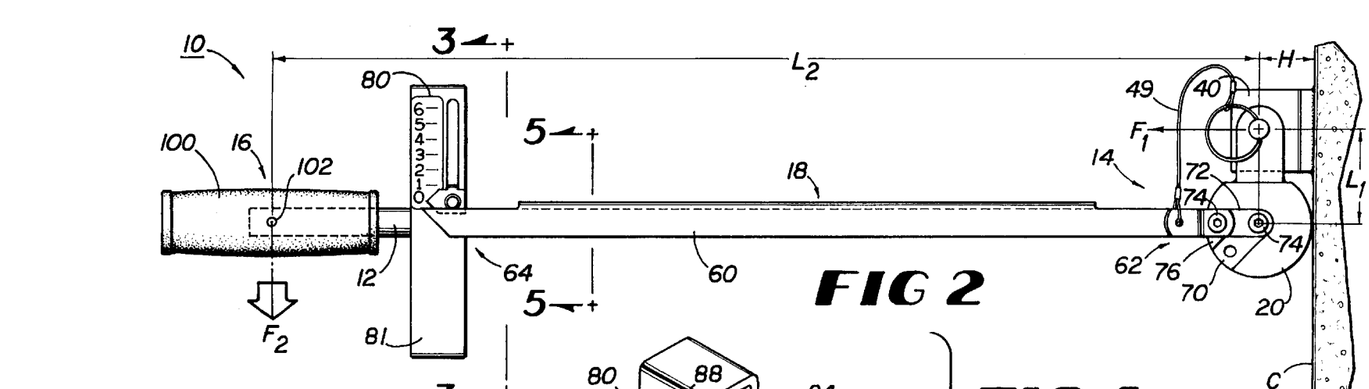
FIG. 2 shows a side view of a testing device used to test the adhesion of a coating to a generally vertical substrate according to a preferred form of the present invention.
Figure 3:
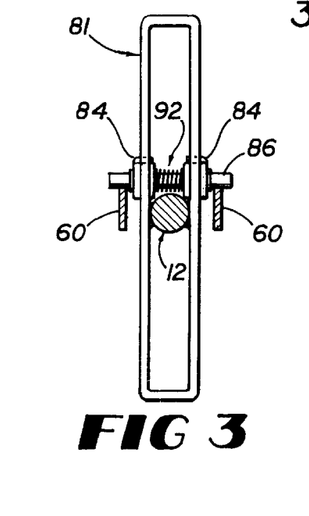
FIG. 3 shows a partial end view, in partial cross-section, of a testing device according to a preferred form of the present invention.
Figures 4, 5, 5A:
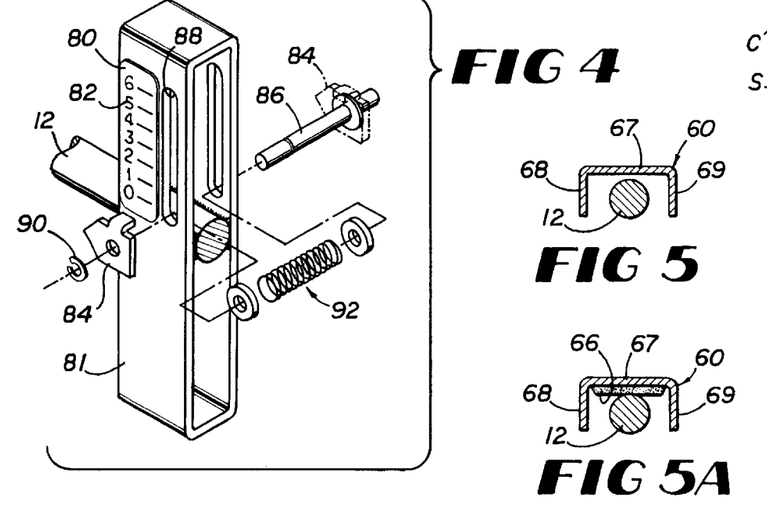
FIG. 4 shows an exploded perspective view of a portion of a testing device according to a preferred form of the present invention.
FIG. 5 shows a partial cross-sectional view of a portion of a testing device according to a preferred form of the present invention.
FIG. 5A shows a partial cross-sectional view of another portion of a testing device according to a preferred form of the present invention.

In the embodiment depicted in FIGS. 1, 1A and 2, a first pointer coupling in the form of a first radial channel 70 formed in at least one of the first and second sides 24, 26 of the contact head 20 engages the first end 62 of the pointer arm 60 in a first pointer position depicted in FIG. 1. A second pointer coupling in the form of a second radial channel 72 can optionally be provided in at least one of the first and second sides 24, 26 of the contact head 20, angularly offset from the first radial channel 70, to engage the first end 62 of the pointer arm 60 in a second pointer position depicted in FIG. 2. The first pointer position is configured to correspond to the first beam position, preferably in a manner whereby the beam 12 and the pointer arm 60 are generally aligned when the beam is relaxed. Similarly, the second pointer position is configured to correspond to the second beam position, preferably in a manner whereby the beam 12 and the pointer arm 60 are generally aligned when the beam is relaxed. Alternatively, the first and second pointer positions can be configured to correspond to the first and second beam positions, respectively, in a manner whereby the beam 12 and pointer arm 60 are offset by a predetermined fixed angle when the beam 12 is relaxed. The offset between the beam 12 and the pointer arm 60 may facilitate calibration, as there will be no possibility of a preset force being applied at the coupling between the beam and the pointer arm, and may also reduce or eliminate potentially damaging impact between the beam and the pointer arm as the flexure of the beam is suddenly released when the test dolly detaches from the substrate. The pointer couplings preferably further comprise one or more releasable fasteners, such as screws or bolts 74. In the embodiment depicted in FIGS. 1–5, a first fastener extends through holes provided in the pointer arm 60 and through the approximate center of the contact head 20, and a second fastener extends through holes provided in the pointer arm 60 and through the contact head 20 in the radial channels 70, 72 adjacent the periphery of the contact head. In preferred form, the first and second radial channels 70, 72 are separately formed in the sides 24, 26 of the contact head 20, whereby a wedge 76 of material comprising the contact head remains to provide structural reinforcement and more precise positioning of the pointer arm 60. Alternatively, the wedge of material can be removed or omitted, and the first and second radial channels 70, 72 can be formed contiguously, as for example by removal of a continuous section of the sides 24, 26, to a predetermined depth and spanning the angle between the first and second radial channels 70, 72. In a particularly preferred embodiment, the first and second pointer positions are offset approximately 45° from one another to facilitate use with horizontal and vertical substrates, as described in greater detail below. One, two, or more pointer couplings can be provided, allowing the pointer arm 60 to be selectively connected to the contact head 20 in any of a plurality of angularly offset positions.

The indicator preferably further comprises a scale 80, which cooperates with the pointer arm 60 for indicating the magnitude of applied force. The scale 80 is preferably mounted to a carriage body 81 mounted on the beam 12 proximal the second end 64 of the pointer arm 60. The scale 80 preferably comprises incremental reference markings 82 adjacent the second end 64 of the pointer arm 60. The indicator can optionally further comprise a position marker 84 for recording a maximum deflection of the device 10 corresponding to the applied detachment force necessary to detach a coating from a substrate. The position marker 84 preferably is carried on a pin 86 slidable within one or more slots 88 provided in the carriage body 81. The slot(s) preferably extend generally perpendicular to the beam 12. A locking ring 90 or other fastening means can be provided to attach the position marker 84 to the pin 86. A spring and washer mechanism 92 or other retention means can be provided to retain the position marker 84 in the position indicating the point of maximum deflection. For example, in the embodiment depicted, the carriage body 81 comprises a generally box-like body having first and second side walls mounted to opposite edges of the beam 12. The pin 86 extends through slots 88 formed in each of the side walls. The pin 86 extends through the spring and washer mechanism 92, to retain the spring and washer mechanism 92 between the side walls. The spring applies an expansion force, pressing the washers against the side walls to frictionally retain the position marker 84 in position. The washers are preferably formed from a hard low-friction plastic. The first and second side legs 68, 69 of the forked second end 64 of the pointer arm 60 straddle the first and second side walls of the carriage body 81, and engage the outwardly-projecting ends of the pin 46 to slide the position marker 84 within the slots 88 as the beam 12 flexes upon application of force when in use as described below. The friction between the washers of the spring and washer mechanism 92 against the inner surfaces of the side walls of the carriage body 81 is overcome by the force applied to the pin 46 by contact with the pointer arm 60, permitting the pointer arm to freely adjust the position the position marker 84 within the slots 88. Upon detachment of the test dolly 40, the flexure of the beam 12 is released, and the friction between the washers of the spring and washer mechanism 92 against the inner surfaces of the side walls of the carriage body 81 retains the position marker 84 in place relative to the scale 80 for observation. First and second scales 80, each having a corresponding position marker 84, can optionally be provided on the first and second side walls, respectively, of the carriage body 81. Optionally, the first scale can indicate detachment force in different units of measurement than the second scale. For example, one of the scales may provide a reading in metric units and the other scale in English units. Alternatively, different scales can be provided for detachment force indication in different ranges corresponding to test dollies having different adhesion surface areas, as discussed in greater detail below. In further preferred and optional embodiments, the scale(s) 80 are adjustably mounted to the carriage body 81, such by means of a projection on the back of the scale 80 carried slidably in a slot provided in the side wall of the carriage body 81, whereby the position of the scale can be adjusted on the carriage body 81 to calibrate the device. Locking means, such as a tamper-proof screw or other coupling or fastener, are preferably provided to releasably fix the position of the scale 80 relative to the carriage body 81 after calibration. In alternate embodiments, the indicator can comprise an electronic or mechanical stress or strain transducer, an electronic or mechanical force indicator, a spring scale, or other means for measuring the extent of bending moment applied to the beam 12 or the force applied to the test dolly.

In further preferred embodiments, the device 10 of the present invention can optionally comprise a handle 100 mounted to the second end 16 of the beam 12. The handle 100 preferably receives the second end 16 of the beam 12 within a bore provided at least partially through the handle. In a still further preferred embodiment, the bore in the handle 100 is sufficiently larger than the second end 16 of the beam 12, whereby there is some measure of play therebetween. A pivot pin 102 attaches the handle 100 to the beam 12, and permits pivotal motion therebetween. In this manner, the application of force to the device 10 is more controlled, reducing any tendency of the user to inadvertently apply a bending force to the beam 12; and the measurement of detachment force of a coating is more precise, as the pivot pin provides a more precise location of the point of application of force to the beam. A handguard 104 can be provided adjacent the handle to protect the user from inadvertently striking the ground upon sudden detachment of a test dolly.

As seen with reference to FIGS. 1, 1A, 6, and 7, in a preferred form of the present invention, the first beam position and first pointer position are generally aligned with one another, and are oriented approximately 135° from the flanges 42 or engagement head 28, whereby the beam 12 and pointer arm 60 are oriented at an angle of approximately 45° to the support surface when the device 10 is in use. This orientation has been found particularly advantageous for testing adhesion of a coating applied to a horizontal substrate. As seen in FIG. 2, the second beam position and the second pointer position are preferably generally aligned with one another, and oriented approximately 90° from the flanges 42 or engagement head 28, whereby the beam 12 and pointer arm 60 are oriented at an angle of approximately 90° to the support surface when the device 10 is in use. This orientation has been found particularly advantageous for testing adhesion of a coating applied to a vertical substrate. Of course, the present invention also encompasses alternate beam and/or pointer positions relative to the engagement means, whereby the beam and/or pointer can be configured in any of a number of orientations when the device is in use. The geometry of the device 10 and the test dolly 40, including in particular the offset distance $L_1$ of the engagement means from the fulcrum of pivotal motion (e.g., the distance from the flange holes 44 to the center of contact head 20, or the distance from the slot 50 to the center of the contact head 20'), and the radius or height H of the test dolly 40 and the contact head 20, 20', are selected so as to apply force to the test dolly in a direction normal to the support surface or substrate. In this manner, in operation, the force applied to the test dolly by the device 10 is substantially entirely in tension, normal to and away from the substrate. This reduces or eliminates any errors in measurement that might otherwise result due to application of shear or peeling forces to a test dolly. The geometry and strength of the device 10 and the test dolly 40, including in particular, the ratio of the offset distance $L_1$ and the moment arm $L_2$ (e.g., the distance from pivot point 102 to the center of the contact head 20, 20'), are selected to permit application of sufficient force $F_1$ to detach the test dolly upon the application of manual force $F_2$ to the handle 100 ($F_1 \times L_1 = F_2 \times L_2$). The stiffness of the beam 12, and the range of the indicator are selected to provide adequate measurement sensitivity in the range of applied forces anticipated in the intended uses of the device 10. Additionally or alternatively, the range of detachment forces capable of being applied by a particular test device 10 can be varied by adjusting the size of the test dolly 40 to increase or decrease the adhesion surface area in adhesive contact with the coated substrate. For example, the adhesion of a coating to a substrate will typically be measured in terms of the tensile stress, or force per unit area (e.g., lbs./in$^2$, kg/mm$^2$, etc.), required to detach the coating from the substrate. Thus, for a given force applied by the device 10 to a test dolly, the effective test range of the device 10 can be increased (i.e., greater applied stress) by decreasing the surface area of the test dolly adhered to the coated substrate. Conversely, the effective test range of the device 10 can be decreased (i.e., lower applied stress) by increasing the surface area of the test dolly adhered to the coated substrate. As discussed above, different scales 80 can optionally be provided for measurement of stresses applied using test dollies of different adhesion contact surface areas.

The present invention also comprises an improved test dolly 40", as seen best with reference to FIG. 8. The test dolly 40" preferably comprises a base portion 140 having a plurality of generally straight sides 140a, 140b, 140c, 140d. In the preferred embodiment depicted, test dolly 40" comprises a generally rectangular, and more preferably, a generally square, base portion 140, having four generally straight sides. In alternate embodiments, a triangular or other straight-sided, polygonal base portion 140, having three or more generally straight sides, can be provided. The base portion 140 preferably comprises a generally planar adhesion contact surface or attachment face 142 for attachment to the coating to be tested. Alternatively, the contact surface 142 can be non-planar for applications wherein the adhesion of a coating applied to a corresponding non-planar substrate is to be tested. An upper surface 144, generally opposite the contact surface 142 tapers from a greater thickness near the center of the dolly 40" to a lesser thickness near the edges of the dolly 40". An engagement fin 146 preferably projects upwardly from the base portion 140, at or near the center of the dolly 40", and preferably includes a generally centrally located hole 148 or other engagement feature for engagement by the device 10. In preferred form, a smooth transition is provided between the engagement fin 146 and the base portion 140 of the dolly 40", as by forming a fillet therebetween, to provide increased strength and rigidity. The edges of the base portion 140 around the contact surface 142 are preferably rounded to prevent stress concentrations in the coating during testing. The dolly 40" is preferably fabricated by forming an extrusion having the desired generally T-shaped cross-sectional geometry, and cutting the extrusion to the desired length. The dolly can be formed of aluminum, steel, or other substantially rigid material. In an example embodiment, the base portion is approximately 1½"×1½", the height of the dolly is approximately 1½", the distance from the contact surface 142 to the center of the hole 148 or other engagement feature is approximately 1", the thickness of the engagement fin 146 is approximately ¼", and the thickness of the base portion 142 tapers from 0.184" to 0.632". Of course, those skilled in the art will recognize that the size and geometry of the test dolly 40" can be varied as needed according to the particular testing application at hand.

The use of a square or other straight-sided test dolly has been found to provide surprisingly superior results, as compared to previously known round test dollies. For example, internal cohesion within the coating material can cause inconsistent or inaccurate test results, typically in the form of erroneously high coating adhesion measurements due to adhesion between the substrate and portions of the coating beyond the periphery of the test dolly. In order to ensure that the test results reflect only the adhesion of the area of coating underneath the test dolly to the substrate, standard testing procedures typically require that the coating be scored about the periphery of the test dolly to isolate the section of coating to be tested from adjacent sections of coating. Of course, those skilled in the art will recognize that scoring around the test dolly may not be necessary in all instances, such as for example in the testing of ultra-thin coatings or coatings having insubstantial internal cohesion, or when the testing procedure takes into account the additional surface area of the detached coating beyond the periphery of the test dolly. Testing using previously known round test dollies generally requires the use of a core drill to score the coating about the dolly. Core drilling typically requires substantial set-up efforts, such as anchoring the base plate of the drilling apparatus to the substrate, and is particularly cumbersome on vertical or uneven substrate surfaces. Also, in many instances a pilot hole must be pre-drilled into the substrate in order to prevent the core drill from "walking" on the test surface. If the coating is scored with a core drill prior to adhesion of the test dolly to the test surface, and the test dolly is affixed to the test surface overlying the pilot hole, inaccurate or inconsistent test results may be obtained if the surface area of the portion of coating that was removed in forming the pilot hole is not taken into consideration in determining the adhesion of the coating to the substrate. This may add to the complexity of the testing procedure and/or of calculation of the coating adhesion. The consistency and/or accuracy of test results may be further adversely affected due to the potential for partial or complete detachment of the coating from the substrate and/or internal failure of the substrate that can result from core drilling. For example, if the core drill is tipped or cocked at an angle during the scoring procedure, the portion of the coating and/or substrate within the core drill can be partially or completely detached from the surrounding substrate. Also, the core drill may impart frictional forces upon the portion of the coating and/or substrate within the core drill that could result in partial or complete detachment from surrounding portions of the substrate. This can be particularly problematic if the test dolly is adhered to the test surface prior to scoring and used as a centering point for the core drill, as the core drilling operation may impart forces on the test dolly resulting in partial or complete detachment from the substrate. Additionally, core drilling equipment may not be readily available on many jobsites. Even if core drilling equipment is available, it may be difficult to find a core drilling bit having an inside diameter closely matching the exterior diameter of the test dolly, as core drilling bits are typically manufactured to have standard nominal outside diameters in order to produce a final hole having a standard nominal dimension.

Many of the disadvantages resulting from the provision of round test dollies are overcome through the provision of a straight-sided test dolly according to the present invention. For example, a side-grinder or saw, preferably equipped with a diamond blade, can advantageously be utilized to score the coating about the periphery of a straight-sided test dolly, either before or after the adhesion of the dolly to the test surface. Saws and side-grinders may be more readily available on many jobsites than are core drills, thus rendering scoring about the improved test dolly 40" of the present invention more convenient than with conventional round dollies. Moreover, it is not necessary to match the dimensions of the tool to those of the test dolly as when scoring using a core drill. Typically, the use of a saw or grinder to score about a test dolly requires little in the way of set-up or surface preparation, regardless of whether the test surface may be uneven, or oriented horizontally, vertically or otherwise. Additionally, it has been found that the use of a saw or grinder to score the coating around a straight-sided test dolly is not as likely to partially or completely detach the coating and or the substrate, or otherwise alter the accuracy or reliability of the test results, as may result from core drilling. In particular, it has been found that the use of a saw or grinder to score about a straight-sided test dolly eliminates or substantially reduces any risk of binding, as may occur between a core drill and the edge of a round test dolly; and also eliminates or substantially reduces any risk of applying torque to the test dolly, as may result from tipping the core drill at an angle when engaged around a round test dolly.

In preferred forms, the testing device 10 of the present invention is formed of metal, plastic, and/or other materials having sufficient strength and rigidity for the intended application. In an example embodiment, the device can be fabricated by modification of a commercially available beam-and-pointer type torque wrench, such as a standard 200 lb. capacity beam type torque wrench. The socket head of a torque wrench can, for example, be replaced by the contact head 20 with attached engagement means. Alternatively, the device 10 can be independently fabricated from raw materials using standard fabrication techniques. For example, commercially available bar or rod stock having the desired specifications, such as for example, diameter, hardness, stiffness, heat treatment, etc., can be cut to the desired length and machined to "tune" the stock to form a beam 12 having the desired flexure. The stock is typically "tuned" by fabricating the beam to be slightly stiffer than desired, and machining the beam to remove sufficient material to reduce the stiffness to the desired point. Likewise, the other components of the device 10, including the contact head 20 and pointer arm 60 can be fabricated from raw materials according to known fabrication techniques. After fabrication and assembly of the components, the device 10 is preferably calibrated by applying a known force or bending moment to the device, adjusting the position of the scale 80 on the carriage body 81 whereby the indicator indicates application of the known force or moment, and affixing the scale in place. It may be necessary to recalibrate the indicator periodically, or upon the occurrence of specified conditions. This can be accomplished by releasing the scale 80, as by loosening a tamper-proof fastener affixing the scale 80 to the carriage body 81, applying a known force or bending moment to the device, adjusting the position of the scale 80 on the carriage body 81 whereby the indicator indicates application of the known force or moment, and re-affixing the scale.

The present invention further comprises a method of testing the adhesion of a coating C to a substrate S. The coating C is first applied to at least a portion of the substrate S that is to be tested, according to standard technique or coating manufacturer specification. After the coating has cured, a testing dolly is attached to the surface of the coating, such as by adhesive bonding using a suitable glue such as a two component epoxy. Excess glue is scraped from around the edges of the dolly, and the glue is allowed to harden. The coating is preferably scored about the periphery of the dolly to prevent the internal cohesion of the coating from affecting the measurement of adhesion between the coating and the substrate. If a straight-sided dolly is utilized, a saw such as a diamond or carbide bladed saw can be utilized to score the coating around the straight sides of the dolly. Alternatively, if a round dolly is used, the coating can be scored around the perimeter of the dolly using a core drill.

The testing device 10 is then coupled to the dolly by engagement of the engagement means of the testing device with the hole, key or other engagement feature of the dolly. For example, in the depicted embodiments, the dolly is coupled to the testing device by insertion of the pin 46 through the hole 48 in the dolly and through the holes 44 in the flanges 42, or by sliding the key 52 of the dolly into the slot 50 of the testing device. If the testing device provides multiple beam and/or pointer positions, the beam and/or pointer arm of the testing device are connected in a selected one of the beam and/or pointer positions provided, as detailed above. Force is then applied by the testing device to the dolly in a direction generally normal the support surface. For example, as shown in FIGS. 1 and 6, upward force can be applied to a dolly attached to a generally horizontal coated substrate by arranging the beam and pointer arm in a first beam position and first pointer position, respectively, whereby when the test dolly is engaged and the contact head is placed in contact with the support surface, the beam is oriented at an acute angle, preferably approximately 45°, to the support surface. Downward manual force is applied to the second end of the beam, preferably through a pivotally mounted handle. The contact point of the contact head with the support surface forms a fulcrum, producing an upward force applied to the dolly. Alternatively, as shown in FIG. 2, outward normal force can be applied to a dolly attached to a generally vertical coated substrate by arranging the beam and pointer arm in a second beam position and second pointer position, respectively, whereby when the test dolly is engaged and the contact head is placed in contact with the support surface below the dolly, the beam is oriented at approximately 90° to the support surface. Downward manual force is applied to the second end of the beam, preferably through a pivotally mounted handle. The contact point of the contact head with the support surface forms a fulcrum, producing an outward force applied to the dolly. Of course, it will be understood that the method of the present invention also encompasses application of force to a test dolly in a direction generally normal to the coated substrate using other orientations of the beam and/or pointer, and/or other directions of application of manual force to the second end of the beam, as may be dictated by the conditions of the testing site or by preferences of the user.

As force is applied to the second end of the beam, the beam flexes, but the pointer arm remains generally straight. The extent of flexure of the beam, as indicated by the position of the pointer arm on the scale or by information provided by an alternative form of indicator, indicates the applied force. Progressively increasing force is applied to the second end of the beam, and thereby to the test dolly, until the amount of force applied to the dolly exceeds the adhesion strength of the coating to the substrate, the adhesion strength of the glue holding the dolly to the coating, or the internal cohesive tensile strength of the substrate, and the dolly breaks loose from the substrate. The test results are preferably reported in either pounds per square inch or kilograms per square centimeter. In addition, the failure mode as observed from the glued face of the dolly is also recorded (failure may be by cohesive failure of the substrate, failure of the bond between the substrate and the coating, cohesive failure of the coating, failure between coats of a multiple coat system or failure of the glue used to bond the dolly to the coating, or any combination of these). By measuring the applied force required to detach the dolly and coating from the substrate, the adhesion value of the coating to the substrate, or other information regarding the coating and/or substrate can be determined. The amount of force applied is preferably determined based on the maximum deflection of the beam just prior to detachment of the dolly, and thereby determining the maximum force applied to the dolly, in a manner similar to that of a beam-and-pointer type torque wrench, with the exception that the device of the present invention measures applied pulling force or tensile stress instead of torque. The provision of a position marker with position retention means, as described above, assists the user in determining the maximum deflection of the beam just prior to detachment of the dolly.

While the invention has been described in its preferred forms, it will be readily apparent to those of ordinary skill in the art that many additions, modifications and deletions can be made thereto without departing from the spirit and scope of the invention.

What is claimed is:

1. A device for testing the adhesion of a coating to a substrate, said device comprising:

a beam having a first end, a second end, and an intermediate portion;

a contact head connected to the first end of said beam;

a pointer arm having a first end connected to the first end of said beam and a second free end opposite the first end;

a scale mounted to said beam proximal the second end of said pointer, whereby bending of said beam in a plane of flexure moves the scale across the pointer arm; and engagement means for releasably engaging a test dolly, said engagement means extending from the contact head in the plane of flexure and angularly offset from the beam.

2. The device of claim 1, wherein said contact head comprises a first beam coupling for engaging the first end of said beam in a first beam position, a first pointer coupling for engaging said pointer arm in a first pointer position corresponding to the first beam position, a second beam coupling for engaging the first end of said beam in a second beam position, and a second pointer coupling for engaging said pointer arm in a second pointer position corresponding to the second beam position.

3. The device of claim 2, wherein said first beam coupling comprises a first hole in said contact head, and said second beam coupling comprises a second hole in said contact head, said first and second holes being angularly offset from one another.

4. The device of claim 3, wherein said contact head comprises a generally cylindrical element having a circumferential face and first and second sides, and wherein said first and second holes are formed in said circumferential face.

5. The device of claim 4, wherein said first pointer coupling comprises a first radial channel formed at least one of said first and second sides, and said second pointer coupling comprises a second radial channel formed at least one of said first and second sides.

6. The device of claim 1, wherein said scale comprises a slot carrying a position marker, said position marker slidable within said slot upon contact with the second end of said pointer arm.

7. The device of claim 1, further comprising a handle pivotally mounted adjacent the second end of said beam.

8. The device of claim 1, wherein said engagement means comprises at least one flange extending from said contact head, each said flange comprising a hole therethough, said engagement means further comprising a pin for removable insertion through the hole of each said flange.

9. The device of claim 1, wherein said engagement means comprises a surface feature adapted to cooperate with a corresponding surface feature of the test dolly.

10. A system for testing the adhesion of a coating to a substrate, said system comprising:

a beam having a first end, a second end, and an intermediate portion;

a contact head connected to the first end of said beam;

a test dolly having a generally planar attachment face for attachment to a coating applied to a substrate;

engagement means connected to said contact head for releasably engaging said test dolly; and an indicator responsive to a degree of flexure of said beam to indicate a magnitude of force applied to said test dolly.

11. The system of claim 10, further comprising a handle pivotally mounted proximal the second end of said beam.

12. The system of claim 10, wherein said contact head is selectively connected to said beam in one of a plurality of angularly offset positions.

13. The system of claim 12, wherein said contact head comprises a first hole for receiving the first end of said beam in a first position, and a second hole for receiving the first end of said beam in a second position angularly offset from the first position.

14. The system of claim 10, wherein said engagement means comprises at least one flange extending from said contact head, each said flange comprising a hole therethough, said engagement means further comprising a pin for removable insertion through the hole of each said flange.

15. The system of claim 10, wherein said engagement means comprises a surface feature adapted to cooperate with a corresponding surface feature of the test dolly.

16. The system of claim 10, wherein said indicator comprises a scale mounted to the intermediate portion of said beam, and wherein said device further comprises a pointer arm having a first end substantially rigidly coupled to the first end of said beam.

17. A method of testing the adhesion of a coating to a substrate, comprising:

attaching a test dolly to a portion of a coating;

coupling a testing device to the test dolly, the testing device comprising a beam, a contact head connected to a first end of the beam, engagement means for engaging the test dolly, and an indicator;

applying sufficient force to a second end of the beam to flex the beam and detach the test dolly and an attached portion of the coating from the substrate; and observing the indicator to determine a measure of adhesion of the coating to the substrate.

18. The method of claim 17, wherein the substrate is generally vertical, and wherein the step of coupling a testing device to the test dolly comprises orienting the beam in a generally horizontal position for applying force to detach the test dolly.

19. The method of claim 17, wherein the substrate is generally horizontal, and wherein the step of coupling a testing device to the test dolly comprises orienting the beam at an acute angle relative to the substrate for applying force to detach the test dolly.

20. The method of claim 17, further comprising the step of coupling the first end of the beam to the contact head in a selected one of a plurality of beam positions.

21. The method of claim 17, further comprising providing a first test dolly having a first surface area for attachment to the coating and a second test dolly having a second surface area for attachment to the coating, the first surface area being greater than the second surface area, whereby application of a greater force is required to detach the first test dolly from the substrate than to detach the second test dolly from the substrate.

22. A test dolly for testing the adhesion of a coating to a substrate, said test dolly comprising:

a base portion comprising an attachment face for adhesion to a portion of a coating, said base portion further comprising a plurality of straight sides; and an engagement feature for attachment to a testing device.

* * * * *